US011754450B2

(12) United States Patent
Hofvander et al.

(10) Patent No.: US 11,754,450 B2
(45) Date of Patent: Sep. 12, 2023

(54) TEMPERATURE SENSING APPARATUS FOR USE WITH A PHOTO-THERMAL TARGETED TREATMENT SYSTEM AND ASSOCIATED METHODS

(71) Applicant: Accure Acne, Inc., Boulder, CO (US)

(72) Inventors: Henrik Hofvander, Budapest (HU); Michael John Estes, Lafayette, CO (US)

(73) Assignee: Accure Acne, Inc., Boulder, CO (US)

( * ) Notice: Subject to any disclaimer, the term of this patent is extended or adjusted under 35 U.S.C. 154(b) by 0 days.

(21) Appl. No.: 17/867,210

(22) Filed: Jul. 18, 2022

(65) Prior Publication Data

US 2022/0357218 A1 Nov. 10, 2022

Related U.S. Application Data

(63) Continuation of application No. 16/734,280, filed on Jan. 3, 2020, now Pat. No. 11,391,634.
(Continued)

(51) Int. Cl.
*G01K 15/00* (2006.01)
*A61N 5/00* (2006.01)
(Continued)

(52) U.S. Cl.
CPC .............. *G01K 15/005* (2013.01); *A61N 5/00* (2013.01); *A61N 5/06* (2013.01); *A61N 5/0616* (2013.01);
(Continued)

(58) Field of Classification Search
CPC ........ G01K 15/005; G01K 1/143; G01K 7/02; A61N 5/00; A61N 5/06; A61N 5/0616;
(Continued)

(56) References Cited

U.S. PATENT DOCUMENTS

| 5,023,459 A | 6/1991 | Osborn et al. |
| 6,190,377 B1 | 2/2001 | Kuzdrall |

(Continued)

FOREIGN PATENT DOCUMENTS

| CN | 103638606 A | 3/2014 |
| CN | 109008966 A | 12/2018 |

(Continued)

OTHER PUBLICATIONS

Extended European Search Report, European Patent Application 19877178.4-1126, dated Jun. 22, 2022.
(Continued)

*Primary Examiner* — Wei (Victor) Y Chan
(74) *Attorney, Agent, or Firm* — Neugeboren O'Dowd PC (57) ABSTRACT

A temperature measurement system for measuring a temperature of a measured surface includes: 1) a first temperature sensor; and 2) a reference surface including a second temperature sensor integrated therein. The first temperature sensor includes a field of view simultaneously covering both at least a portion of the measured surface and at least a portion of the reference surface, thus is configured for simultaneously taking a first measurement of both the portion of the measured surface and the portion of the reference surface. The first measurement of the reference surface taken by the first temperature sensor is compared to a second measurement taken by the second temperature sensor for use in calibrating the first temperature sensor.

21 Claims, 5 Drawing Sheets

Related U.S. Application Data (60) Provisional application No. 62/804,719, filed on Feb. 12, 2019.

(51) Int. Cl.
| | |
|---|---|
| *A61N 5/06* | (2006.01) |
| *G01K 1/143* | (2021.01) |
| *G01J 5/00* | (2022.01) |
| *G01K 7/02* | (2021.01) |
| *G01K 7/22* | (2006.01) |
| *A61B 90/00* | (2016.01) |
| *A61B 3/00* | (2006.01) |

(52) U.S. Cl.
CPC ............... *G01J 5/00* (2013.01); *G01K 1/143* (2013.01); *A61B 3/0008* (2013.01); *A61B 90/361* (2016.02); *A61B 2562/0271* (2013.01); *A61B 2562/14* (2013.01); *G01K 7/02* (2013.01); *G01K 7/22* (2013.01)

(58) Field of Classification Search
CPC ........ G01J 5/00; A61B 90/361; A61B 3/0008; A61B 2562/0271; A61B 2562/14
See application file for complete search history.

(56) References Cited

U.S. PATENT DOCUMENTS

| | | |
|---|---|---|
| 2004/0254472 A1 | 12/2004 | McQuilkin |
| 2007/0138394 A1* | 6/2007 | Lane .................. G01J 5/0803 250/353 |
| 2007/0153871 A1 | 7/2007 | Fraden |
| 2010/0290500 A1 | 11/2010 | Zettler et al. |
| 2011/0228811 A1 | 9/2011 | Fraden |
| 2013/0223472 A1 | 8/2013 | Maston |
| 2014/0121631 A1 | 5/2014 | Bean et al. |
| 2015/0316473 A1 | 11/2015 | Kester et al. |
| 2015/0355030 A1 | 12/2015 | Au et al. |
| 2016/0320252 A1 | 11/2016 | Ostermeyer et al. |
| 2017/0014186 A1 | 1/2017 | Chen et al. |

FOREIGN PATENT DOCUMENTS

| | | |
|---|---|---|
| CN | 109073472 A | 12/2018 |
| DE | 10346993 A1 | 6/2005 |
| EP | 0747682 A1 | 12/1996 |
| EP | 3093637 B1 | 11/2021 |
| GB | 2410690 A | 8/2005 |
| JP | H09250955 A | 9/1997 |
| JP | H10111172 A | 4/1998 |
| JP | 2007516018 | 8/2007 |
| JP | 2011022039 A | 2/2011 |
| JP | 2017215274 A | 12/2017 |
| KR | 20060012649 A | 2/2006 |
| KR | 1020180058293 A | 6/2018 |
| RU | 2774735 C1 | 6/2022 |
| TW | 201743033 A | 12/2017 |
| WO | 2004097389 A2 | 11/2004 |
| WO | 2017003707 A1 | 1/2017 |
| WO | 2018022001 A1 | 2/2018 |
| WO | 2020167389 A1 | 8/2020 |

OTHER PUBLICATIONS

Israeli Patent Application 285240, Notice of Allowance, dated Aug. 30, 2022.
Japanese Patent Application 2021-545767, First Office Action, dated Sep. 16, 2022.
China Patent Office, "First Office Action for Chinese Application 202080013969.9," dated Oct. 20, 2022, pp. 32, Published in CN.
KIPO, "Office Action for Korean Application No. 10-2021-7028536," dated Jan. 4, 2023, pp. 12; Published in: KR.
Mexican Institute of Industrial Property, "Letters Patent for Mexican Patent No. 397280," granted Nov. 9, 2022, pp. 47, Published in: MX.
Nickitas-Etienne, Athina, "International Preliminary Report on Patentability of PCT Application No. PCT/US20/12473," dated Aug. 10, 2021, pp. 7, Published in US.
Russian Patent and Trademark Office (RUPTO) "Decision to Grant a Patent for Russian Application No. 2021126686/28," dated May 30, 2022, pp. 20.
Russian Patent and Trademark Office (RUPTO), "Notification on violation of unity of invention and Search Report for Russian Application No. 2021126686/28," dated Jan. 28, 2022, pp. 23.
Russian Patent and Trademark Office (RUPTO), "Office action of substantive examination of Russian Application No. 2022116200/28," dated Feb. 1, 2023, pp. 8.
Russian Patent and Trademark Office (RUPTO), "Search Report for Russian Application No. 2022116200/28," dated Feb. 1, 2023, pp. 6.
Thomas, Shane, "The International Search Report and the Written Opinion of the International Searching Authority for PCT application No. PCT/US20/12473," dated Mar. 18, 2020, pp. 10, Published in US.
Vieira de Moraes Junior, Manoel Carlos, "Search Report of Brazilian Application No. BR112021013959-1, " dated Mar. 27, 2023, pp. 2, Published in BR.
Vieira de Moraes Junior, Manoel Carlos, "Technical Examination Report of Brazil Application No. BR112021013959-1," dated Mar. 27, 2023, pp. 5, Published in BR.
European Patent Office, Supplementary Partial European Search Report for European Patent Application EP20755483; completed Sep. 30, 2022; dated Oct. 12, 2022; 18 pages.
Li Wang et al.; Types of thermal imaging systems for mass fever screening and their evaluations; Thermosense XXVI; Proc. of SPIE, vol. 5405; (2004).
Canadian Patent Office; First Office Action for Canadian Patent Application 3,127,861; dated Sep. 23, 2022; 8 pages.

* cited by examiner

TEMPERATURE SENSING APPARATUS FOR USE WITH A PHOTO-THERMAL TARGETED TREATMENT SYSTEM AND ASSOCIATED METHODS

PRIORITY CLAIM

The present application is a continuation of copending U.S. patent application Ser. No. 16/734,280, filed Jan. 3, 2020 and entitled "Temperature Sensing Apparatus for Use with a Photo-Thermal Targeted Treatment System and Associated Methods," which claims the benefit of U.S. Provisional Patent Application Ser. No. 62/804,719, filed Feb. 12, 2019 and entitled "Temperature Sensing Apparatus for Use with a Photo-Thermal Targeted Treatment System and Associated Methods," both of which applications are incorporated herein by reference in their entirety.

FIELD OF THE INVENTION

The present invention relates to energy-based treatments and, more specifically, systems and methods for improving the accuracy of temperature measurements used during an energy-based dermatological treatment.

BACKGROUND OF THE INVENTION

Sebaceous glands and other chromophores embedded in a medium such as the dermis, can be thermally damaged by heating the chromophore with a targeted light source, such as a laser. However, the application of enough thermal energy to damage the chromophore can also be damaging to the surrounding dermis and the overlying epidermis, thus leading to epidermis and dermis damage as well as pain to the patient.

Previous approaches to prevent epidermis and dermis damage, as well as patient pain include:

1. Cooling the epidermis, then applying the photo-thermal treatment; and
2. Cool the epidermis, also condition (i.e., preheat) the epidermis and dermis in a preheating protocol, then apply photo-thermal treatment in a distinct treatment protocol. In certain instances, the preheating protocol and the treatment protocol are performed by the same laser, although the two protocols involve different laser settings and application protocols, thus leading to further complexity in the treatment protocol and equipment.

For either of these approaches, as well as in many energy-based dermatological procedures, measuring the temperature of the skin surface during the treatment provides valuable information that can be used to adjust the treatment protocol and/or equipment settings in real time. For example, there are contact-less temperature measurement methods, such as those based on optical and imaging techniques, that provide useful avenues for measuring skin surface temperatures during dermatological procedures.

However, accurate contact-less measurements of the skin surface are challenging to perform, particularly when the dermatological procedure involves external mechanisms that can affect the temperature measurement apparatus as well as the skin temperature. For instance, the use of air cooling prior to and during the dermatological procedure can cool the skin surface as well as impact the performance of the sensor that is making the contact-less skin surface measurement.

As an example, one approach to make contact-less skin surface temperature measurements is to utilize a multi-pixel infrared (IR) sensor, such as an IR camera. For IR cameras, the measurement uniformity (i.e., the difference in temperature measured by different pixels of the IR camera when viewing a surface with a uniform temperature) is quite good. However, the absolute accuracy (i.e., the absolute recorded value of the temperature measured by each pixel or by averaging the measurements recorded by several adjacent pixels) has a measurement error that may prohibit the use of a contact-less sensor for skin surface measurements. For instance, even the most sophisticated IR cameras are subject to poor absolute accuracy, where a surface measured as 5° C. is actually at 8° C. due to a calibration offset error in the camera.

Another inaccuracy phenomenon is "camera drift" where the accuracy of the camera varies over time, such as due to changes in the overall environmental temperature of the environment in which the procedure is taking place, or for reasons related to the dermatological procedure, such as when, over time, a laser source heats the structure onto which the camera is mounted or when spill-over air from air cooling impinges on the camera and affects the temperature of the camera body, which in turn leads to a measurement error.

SUMMARY OF THE INVENTION

In accordance with the embodiments described herein, there is disclosed a temperature measurement system for measuring a temperature of a measured surface. The system includes: 1) a first temperature sensor; and 2) a reference surface including a second temperature sensor integrated therein. The first temperature sensor includes a field of view simultaneously covering both at least a portion of the measured surface and at least a portion of the reference surface, thus is configured for simultaneously taking a first measurement of both the portion of the measured surface and the portion of the reference surface.

The first measurement of the reference surface taken by the first temperature sensor is compared to a second measurement taken by the second temperature sensor for use in calibrating the first temperature sensor. In an example, the second temperature sensor includes one or more individual sensors in the cases where redundancy is desired, for instance. The first measurement is then adjusted using the reading made by the second temperature sensor.

In accordance with another embodiment, a photo-thermal targeted treatment system for targeting a chromophore embedded in a medium includes a controller; a photo-thermal treatment unit; and a temperature measurement system for measuring a temperature of a measured surface covering at least a portion of the medium. The controller is configured for administering a treatment protocol using the photo-thermal treatment unit. The temperature measurement system includes 1) a first temperature sensor, and 2) a reference surface with a second temperature sensor integrated therein, wherein the first temperature sensor includes a field of view simultaneously covering both at least a portion of the measured surface and at least a portion of the reference surface.

In accordance with yet another embodiment, a method for continuously calibrating a temperature measurement system for use with a dermatological treatment includes: 1) using a first temperature sensor, simultaneously taking a first measurement of a measured surface and a first reference measurement of a reference surface; 2) using a second temperature sensor embedded within a reference surface, taking a second reference measurement of the reference surface; 3)

calculating a comparison value between the first and second reference measurements; and 4) calibrating the first temperature sensor in accordance with the comparison value.

DETAILED DESCRIPTION OF EMBODIMENTS OF THE INVENTION

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity. Like numbers refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items, and may be abbreviated as "/".

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when an element is referred to as being "directly on," "directly connected to," "directly coupled to," or "immediately adjacent to" another element or layer, there are no intervening elements or layers present. Likewise, when light is received or provided "from" one element, it can be received or provided directly from that element or from an intervening element. On the other hand, when light is received or provided "directly from" one element, there are no intervening elements present.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

In laser treatment of acne, the operating thermal range is generally bound on the upper end at the epidermis and dermis damage threshold temperature of approximately 55° C., and at the lower end by the temperature required to bring the sebaceous gland to its damage threshold temperature of approximately 55° C. Based on clinical data, the operating temperature range for acne treatment expressed in terminal skin surface temperature is approx. 45° C. to 55° C., as an example. At skin surface temperatures below 45° C., it has been determined that there is no damage to the sebaceous gland. When the skin surface temperature is between 45° C. and 55° C., there are varying degrees of sebaceous gland damage, with no epidermal damage. Above 55° C., there is epidermal damage in addition to damage to the sebaceous gland.

While there is not a good way to directly measure the temperature of the sebaceous gland being targeted by the treatment protocol, the skin surface temperature can be an indicator of the sebaceous gland temperature. A correlation model providing the correspondence between sebaceous gland temperature and skin surface temperature can then be used to tailor the actual treatment protocol using skin surface temperature measurements for effectively targeting sebaceous gland damage while staying below the damage threshold for the epidermis and dermis. The correlation model can be developed using, for example, an analytical heat transfer model, or by using clinical data (e.g., via biopsies) correlating skin surface temperature to sebaceous gland damage given the application of a specific treatment protocol.

However, while such correlation models can be incorporated into the treatment protocols, the effectiveness and safety of the treatment are still predicated on the accuracy of the skin surface temperature measurement. As mentioned above, there are various contactless methods of measuring skin surface temperature during, for example, dermatological procedures. Devices such as infrared (IR) cameras, pyrometers, bolometers, and dual-wavelength sensors can provide a reading of the skin surface temperature. However, for procedures such as photo-thermal targeted treatment to cause thermal damage to subcutaneous sebaceous glands, accurate, calibrated reading of the skin surface temperature can prevent damage to the epidermis and dermis in and around the treatment area.

The system and associated methods described herein provides a fast, inexpensive, and compact system and method to significantly improve the accuracy of contactless temperature measurements. While much of the discussion below refers to the use of an IR camera as the temperature sensor, any suitable contactless temperature measurement device can be substituted for the IR camera and fall within the scope of the present disclosure.

Figure 1:
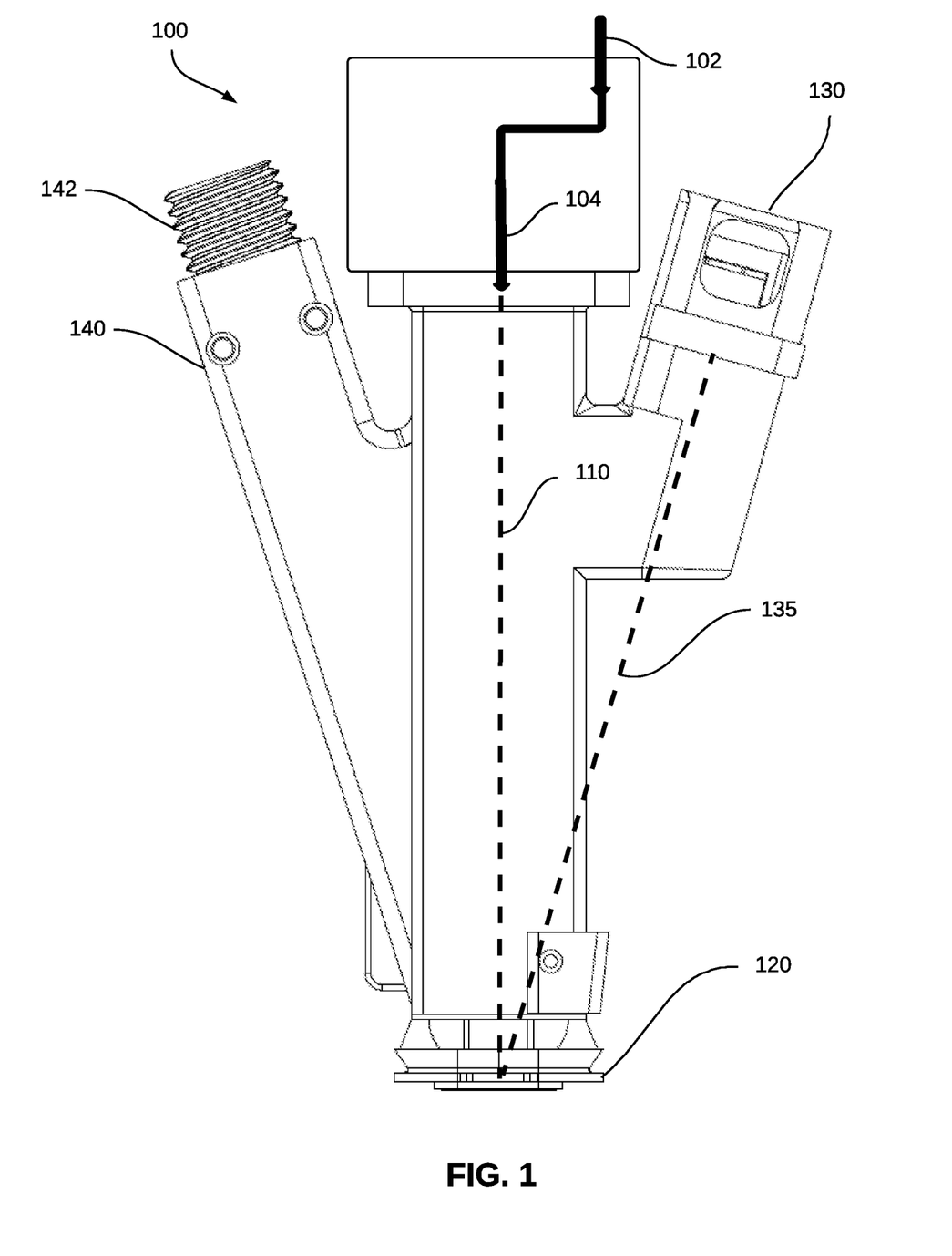
FIG. 1 illustrates a partial cutaway view of a portion of a scanner apparatus suitable for use with a photo-thermal treatment system, in accordance with an embodiment

Turning now to the figures, FIG. 1 illustrates a side view of a portion of a scanner apparatus suitable for use with a photo-thermal treatment system, in accordance with an embodiment. A scanner 100 includes an optical fiber 102 for transmitting a laser beam 104 from a base station (not shown) along an laser beam path 110 toward a treatment tip 120, which is placed in contact with the treatment location. Scanner 100 can optionally include optical components for shaping the light beam projected onto the skin at treatment tip 120. Treatment tip 120 serves as a visual guide for the user to position scanner 100 at a desired treatment location. In order to allow contactless temperature measurement, an IR camera 130 is attached to scanner 100 and pointing downward toward treatment tip 120 such that IR camera 130 is able to detect the temperature of the treatment location along an optical path 135. In an embodiment, IR camera 130 has a fast time response of less than 40 milliseconds between consecutive surface temperature measurements. Additionally, in the embodiment shown in FIG. 1, scanner 100 includes a cooling air duct 140. As an example, an air hose (not shown) can be attached to cooling air duct 140 via a threaded opening 142.

Figure 2:
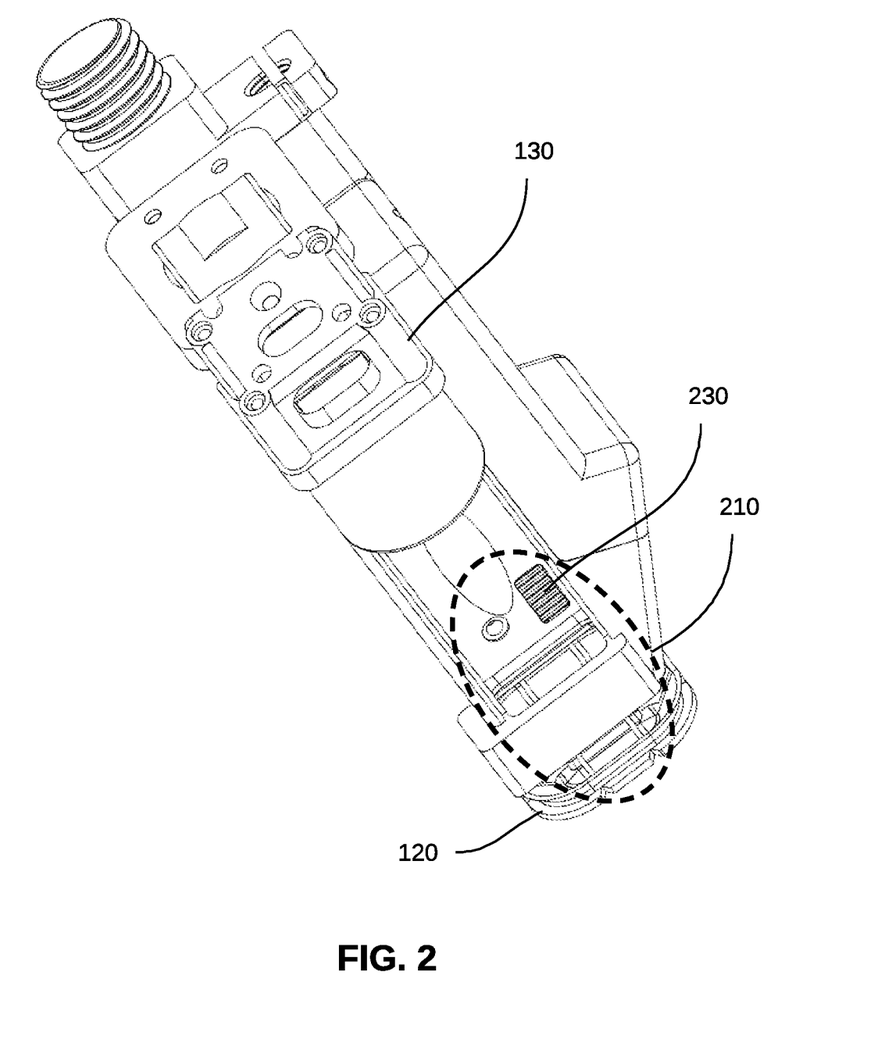
FIG. 2 is a diagram illustrating a field of view (FoV) of a thermal sensor, in accordance with an embodiment.

FIG. 2 illustrates a field of view (FoV) of IR camera 130 looking toward treatment tip 120. FoV 210 (represented by an oval) of the IR camera, in accordance with an embodiment. Visible within FoV 210 are treatment tip 120 and a reference surface 230, attached to an inner surface of scanner 100. Thus, IR camera 130 is capable of simultaneously measuring the temperature of treatment area 222 and reference surface 230.

Figure 3:
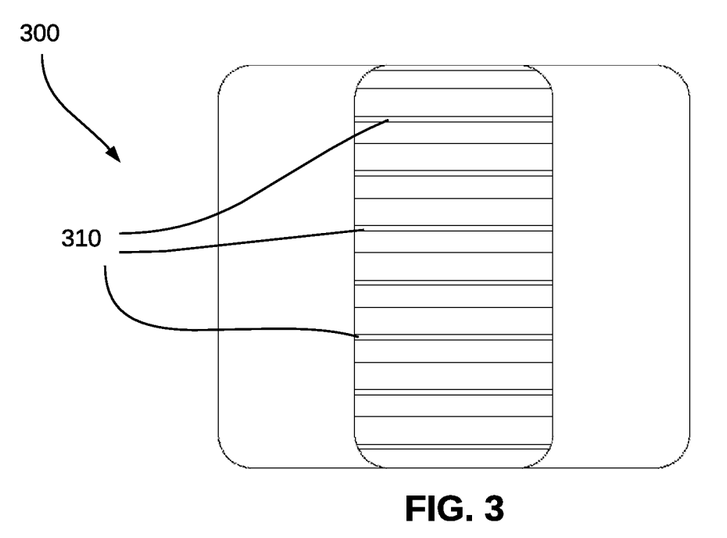
FIG. 3 is a front view of a reference surface for use with a photo-thermal treatment system, in accordance with an embodiment.
Figure 4:
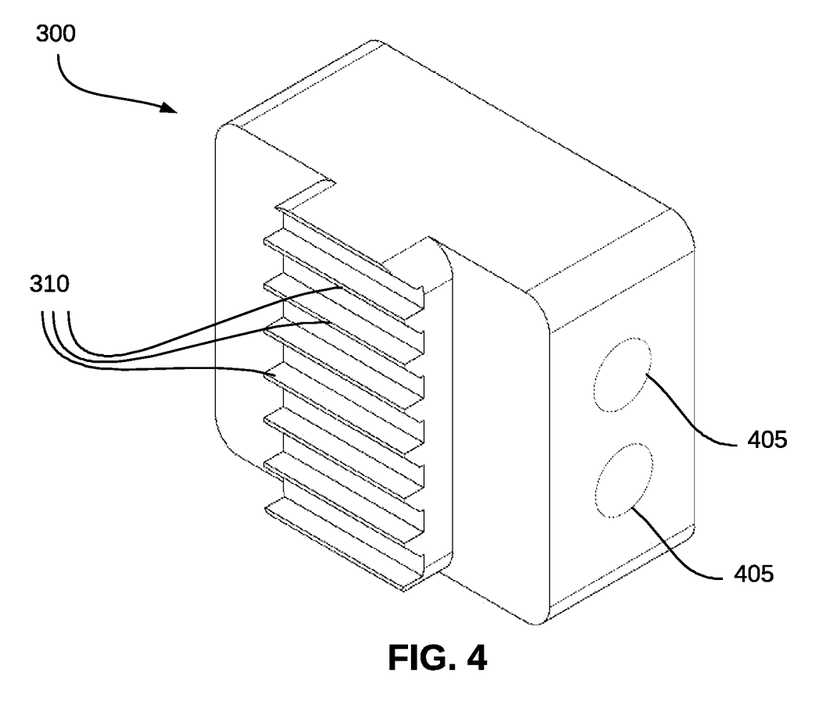
FIG. 4 is an ISO view of the reference surface, as viewed diagonally from the bottom, in accordance with an embodiment.

Further details of the reference surface, in accordance with an embodiment, are illustrated in FIGS. 3-6. FIG. 3 is a front view of a reference surface and FIG. 4 is an ISO view of the reference surface, as viewed diagonally from the bottom, in accordance with an embodiment. As shown in FIGS. 3 and 4, a front surface of reference surface 300 includes a texture 310, which steers reflections and stray light from any surface other, than the reference surface itself, away from FoV 210. In an exemplary embodiment, reference surface 300 also includes one or more mounting holes (not shown) through which reference surface 300 can be attached to, for example, an inside surface of scanner 100 as shown in FIG. 2. Alternatively, reference surface 300 is captively attached or otherwise mounted onto an appropriate location within the FoV of the IR camera. In an embodiment, the reference surface is characterized by a reference emissivity value approximately equal to a measured emissivity value of the measured skin surface. In another example, a surface coating on the reference surface exhibits a light scattering property that is approximately Lambertian, not specular.

Also, as visible in the example illustrated in FIG. 4, reference surface 300 includes one or more insertion holes 405 into which a contact temperature sensor (not shown), such as an integrated circuit temperature measurement device, a resistive temperature detector, a thermocouple, or a thermistor, is placed for directly measuring the temperature of reference surface 300. Alternatively, a contact temperature sensor can be directly attached or otherwise integrated into reference surface 300. The contact temperature sensor can be in direct contact with the reference surface and, in an embodiment, the contact temperature sensor is embedded into the reference surface. Suitable direct contact temperature sensors include thermistors, and should be chosen to provide highly accurate temperature measurements with low noise and low drift. In an embodiment, the contact temperature sensor exhibits high measurement accuracy (e.g., accurate to within 0.1° C.). The contact temperature sensor should have good thermal contact with the reference surface. For example, thermal paste or thermal adhesive is used between the contact temperature sensor and the reference surface such that the temperature measurement by the contact temperature sensor closely corresponds to the temperature of the reference surface. In an embodiment, the reference surface is formed of a material with high thermal conductivity, such as copper or aluminum, such that the reference surface temperature as measured by the IR camera is substantially equal to the internal temperature of the reference surface as measured by the contact temperature sensor.

Figure 5:
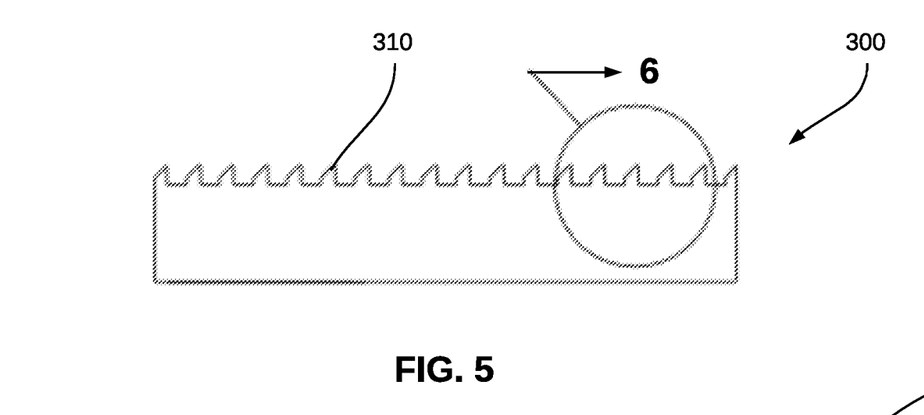
FIG. 5 is a side view of the reference surface, in accordance with an embodiment.

FIG. 5 is a side view of the reference surface, in accordance with an embodiment. As can be seen in FIG. 5, texture 310 has a sawtooth shape in this exemplary embodiment. If a flat, smooth reference surface is used, reflections from other surfaces may bounce off the reference surface and enter the field of view of the camera, thus potentially causing a temperature measurement error. By including a texturing on a front surface of the reference surface, any reflections from outside surfaces are directed away from the FoV of the IR camera such that the camera only sees the reference surface itself along with the treatment area.

Figure 6:
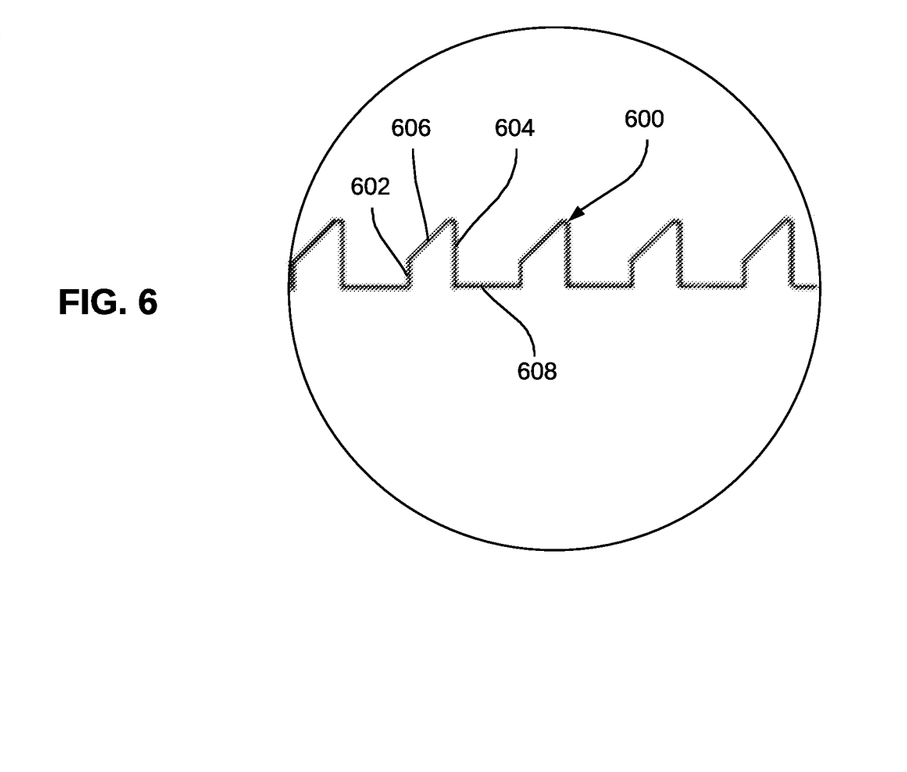
FIG. 6 is an enlarged view of an inset of the reference surface of FIG. 5.

Further details of texture 310 are shown in FIG. 6, which shows an enlarged view of an inset of the reference surface of FIG. 5. As shown in FIG. 6, each sawtooth feature 600 of texture 310 includes a first height 602, a second height 604 and an angled surface 606, and the sawtooth features are separated by a distance 608. First height 602, second height 604, angled surface 606, and distance 608 are configured such that the collective structure serves as a light baffle and/or reflector for directing stray light away from FoV 210. It is noted that other textures are also contemplated, such as textures used in beam traps, light baffles, and laser beam dumps.

As an alternative, the temperature measurement system can also be arranged such that the first temperature sensor periodically measures the temperature of the reference surface in certain time intervals. For example, the reference surface can be included in the field of view of the first temperature sensor as described above, or periodic measurement of the reference surface temperature can be made by the first temperature sensor by scanning the field of view of the temperature sensor using, for example, a scanning mirror located in between the first temperature sensor and the measured surface.

Figure 7:
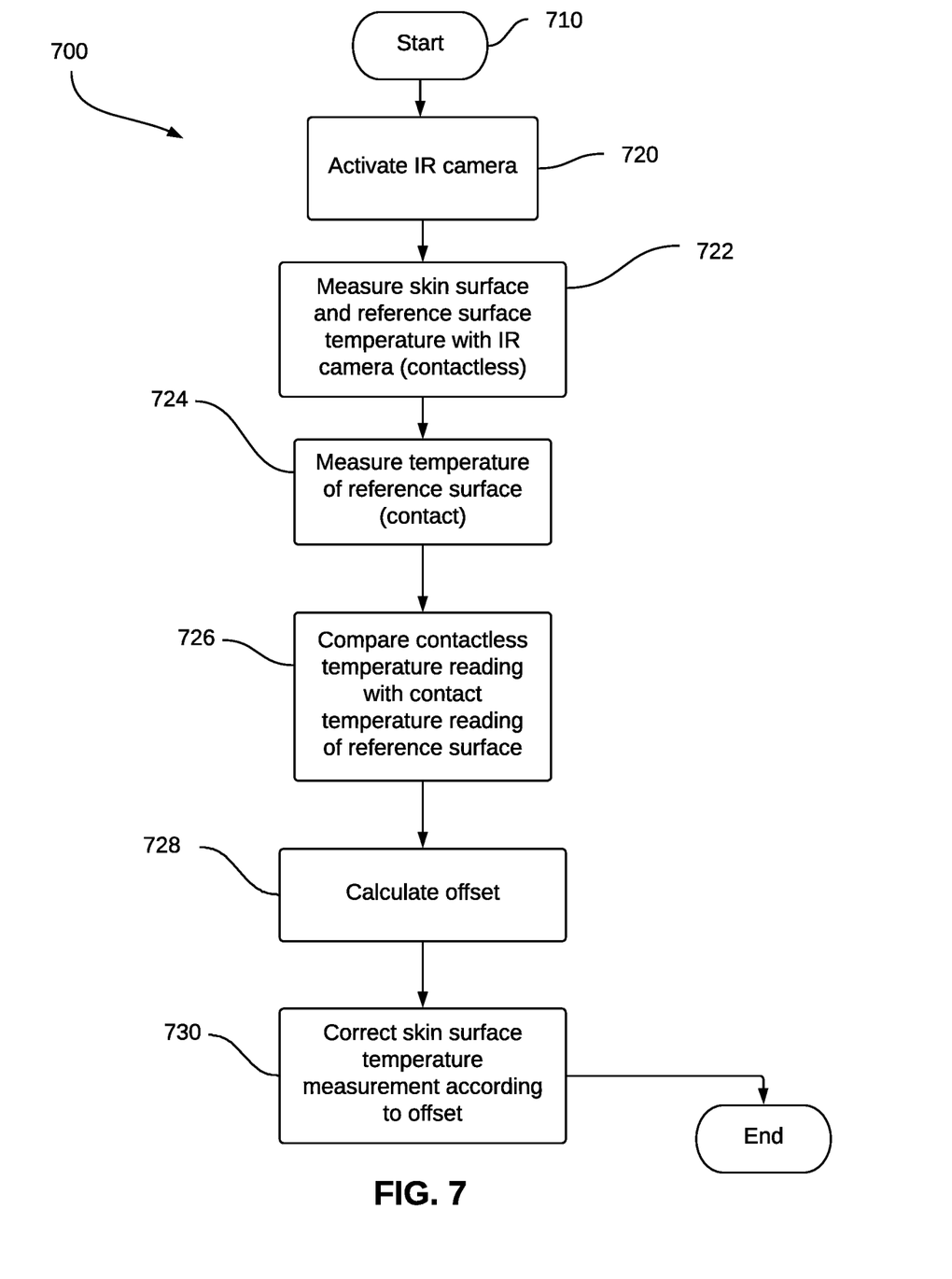
FIG. 7 is a flow diagram illustrating an exemplary contactless method of sensing the temperature of the skin surface, in accordance with an embodiment.

FIG. 7 is a flow diagram illustrating an exemplary contactless method of sensing the temperature of the skin surface, in accordance with an embodiment. As shown in FIG. 7, a process 700 begins with a start step 710, in which the temperature sensing protocol is activated. Then, in a step 720, an IR camera in a setup such as shown in FIG. 1 is activated. IR camera then measures the skin surface temperature and the reference surface temperature in a step 722. It is noted that some IR cameras have an internal self-correction/calibration/shutter mechanism. One such self-correction is a so-called "flat field correction," which ensures that each pixel in the camera measures the same temperature of a constant-temperature surface. The method described in FIG. 7 uses a reference surface that is provided externally to the IR camera. In parallel, a temperature reading of the reference surface is taken with the contact sensor within the reference surface in a step 724. In a step 726, the reference surface temperature taken by the IR camera in step 722 is compared with the temperature reading of the reference surface taken with the contact sensor within the reference surface in step 724. An offset, if any, between the temperature measured in step 722 and the reading taken in step 724 is calculated in a step 728. In a step 730, the offset calculated in 728 is used to correct the skin surface temperature measurement taken by the IR camera. Process 700 is ended in an end step 740.

In other words, by comparing the reference surface temperature, as measured by the contact-less sensor, with a known, high accuracy contact measurement taken of the same reference surface, an offset is calculated, which is used to correct the temperature reading of the skin surface. As a result, the accuracy of the contact-less measurement is greatly improved, regardless of the specific treatment protocol, skin cooling procedures, patient parameters (e.g., age, gender, ethnicity, specific treatment location). It is noted that the contact temperature measurement taken in step 724 of process 700 does not need to occur with every contactless temperature measurement taken in 722. For example, after the offset has been calculated once, steps 724, 726, 728, and 730 can be performed periodically to correct for potential calibration errors.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention.

Accordingly, many different embodiments stem from the above description and the drawings. It will be understood that it would be unduly repetitious and obfuscating to literally describe and illustrate every combination and sub-combination of these embodiments. As such, the present specification, including the drawings, shall be construed to constitute a complete written description of all combinations and subcombinations of the embodiments described herein, and of the manner and process of making and using them, and shall support claims to any such combination or sub-combination.

For example, embodiments such as the below are contemplated:

1. A scanner arrangement for a temperature measurement system for measuring a temperature of a measured surface, the scanner arrangement including: 1) a first temperature sensor; and 2) a reference surface including a second temperature sensor integrated therein. The first temperature sensor includes a field of view simultaneously covering both at least a portion of the measured surface and at least a portion of the reference surface, thus is configured for simultaneously taking a first measurement of both the portion of the measured surface and the portion of the reference surface. The first measurement of the reference surface taken by the first temperature sensor is compared to a second measurement taken by the second temperature sensor for use in calibrating the first temperature sensor.

2. The scanner arrangement of Item 1, wherein the first temperature sensor is an infrared camera.

3. The scanner arrangement of Item 1, wherein the second temperature sensor is a contact sensor.

4. The scanner arrangement of Item 3, wherein the contact sensor includes at least one of an integrated circuit temperature measurement device, a resistive temperature detector, a thermocouple, and a thermistor.

5. The scanner arrangement of Item 1, wherein the reference surface includes a texture thereon.

6. The scanner arrangement of Item 5, wherein the texture is configured for directing any outside surface, other than from the reference surface, away from the field of view of the first temperature sensor.

7. The scanner arrangement of Item 6, wherein the texture includes a sawtooth pattern.

8. The scanner arrangement of Item 1, wherein the reference surface is characterized by a reference emissivity value approximately equal to a measured emissivity value of the measured surface.

9. The scanner arrangement of Item 8, wherein the reference surface is formed of a material characterized by the reference emissivity value.

10. The scanner arrangement of Item 8, wherein the reference surface is coated with a material characterized by the reference emissivity value.

11. The scanner arrangement of Item 1, wherein the reference surface includes a temperature stabilization mechanism.

12. The scanner arrangement of Item 1, further including a second reference surface including a third temperature sensor integrated therein.

13. A photo-thermal targeted treatment system for targeting a chromophore embedded in a medium, the system including a controller; a photo-thermal treatment unit; and a temperature measurement system for measuring a temperature of a measured surface covering at least a portion of the medium. The controller is configured for administering a treatment protocol using the photo-thermal treatment unit. The temperature measurement system includes 1) a first temperature sensor, and 2) a reference surface with a second temperature sensor integrated therein, wherein the first temperature sensor includes a field of view covering both at least a portion of the measured surface and at least a portion of the reference surface.

14. The photo-thermal targeted treatment system of Item 13, wherein a first measurement taken by the first temperature sensor is compared to a second measurement taken by the second temperature sensor for use in calibrating the first temperature measurement with respect to the second temperature measurement.

15. The photo-thermal targeted treatment system of Item 14, wherein the first and second measurements are taken in situ during the treatment protocol.

16. The photo-thermal targeted treatment system of Item 15, wherein the first and second measurements are used by the controller to modify the treatment protocol in progress.

17. The photo-thermal targeted treatment system of Item 16, wherein the first and second measurements are used by the controller to modify an initialization timing of the treatment protocol in accordance therewith.

18. The photo-thermal targeted treatment system of Item 16, wherein the first and second measurements are used by the controller to terminate the treatment protocol in accordance therewith.

19. The photo-thermal targeted treatment system of Item 13, wherein the reference surface includes a texture thereon.

20. The photo-thermal targeted treatment system of Item 19, wherein the texture is configured for directing radiation, other than from the reference surface, away from the field of view of the first temperature sensor.

21. The photo-thermal targeted treatment system of Item 20, wherein the texture includes a sawtooth pattern.

22. The photo-thermal targeted treatment system of Item 13, wherein the temperature measurement system is integrated into the photo-thermal treatment unit.

23. The photo-thermal targeted treatment system of Item 13, wherein a time response of the measured surface temperature (i.e., epidermis temperature) is used to estimate the underlying dermis temperature, thereby providing a more accurate estimate of temperature of the sebaceous gland targeted by the photo-thermal targeted treatment system.

24. A method for continuously calibrating a temperature measurement system for use with a dermatological treatment, the method including: 1) using a first temperature sensor, simultaneously taking a first measurement of a measured surface and a first reference measurement of a reference surface; 2) using a second temperature sensor embedded within a reference surface, taking a second reference measurement of the reference surface; 3) calculating a comparison value between the first and second reference measurements; and 4) calibrating the first temperature sensor in accordance with the comparison value.

In the specification, there have been disclosed embodiments of the invention and, although specific terms are employed, they are used in a generic and descriptive sense only and not for purposes of limitation. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A scanner arrangement for a temperature measurement system for measuring a temperature of a measured surface, the scanner arrangement comprising:
   1) A first temperature sensor; and
   2) a reference surface including a second temperature sensor integrated therein,
   wherein the first temperature sensor includes a field of view simultaneously covering both at least a portion of the measured surface and at least a portion of the reference surface,
   wherein the first temperature sensor is configured for simultaneously taking a first measurement of both the portion of the measured surface and the portion of the reference surface, and
   wherein the first measurement of the reference surface taken by the first temperature sensor is compared to a second measurement taken by the second temperature sensor for use in calibrating the first temperature sensor,
   wherein the reference surface includes a texture thereon, and
   wherein the texture is configured for directing reflections from any outside surface, other than from the reference surface, away from the field of view of the first temperature sensor.

2. The scanner arrangement of claim 1, wherein the first temperature sensor is an infrared camera.

3. The scanner arrangement of claim 1, wherein the second temperature sensor is a contact sensor.

4. The scanner arrangement of claim 3, wherein the contact sensor includes at least one of an integrated circuit temperature measurement device, a resistive temperature detector, a thermocouple, and a thermistor.

5. The scanner arrangement of claim 3, wherein the second temperature sensor includes at least two contact sensors.

6. The scanner arrangement of claim 1, wherein the texture includes a sawtooth pattern.

7. The scanner arrangement of claim 1, wherein the reference surface is characterized by a reference emissivity value approximately equal to a measured emissivity value of the measured surface.

8. The scanner arrangement of claim 7, wherein the reference surface is formed of a material characterized by the reference emissivity value.

9. The scanner arrangement of claim 7, wherein the reference surface is coated with a material characterized by the reference emissivity value.

10. The scanner arrangement of claim 1, wherein the reference surface includes a temperature stabilization mechanism.

11. The scanner arrangement of claim 1, further including a second reference surface including a third temperature sensor integrated therein.

12. A photo-thermal targeted treatment system for targeting a chromophore embedded in a medium, the photo-thermal targeted treatment system comprising:
   a controller;
   a photo-thermal treatment unit; and a temperature measurement system for measuring a temperature of a measured surface covering at least a portion of the medium, wherein the controller is configured for administering a treatment protocol using the photo-thermal treatment unit, wherein the temperature measurement system includes 1) a first temperature sensor, and 2) a reference surface with a second temperature sensor integrated therein, and wherein the first temperature sensor includes a field of view covering both at least a portion of the measured surface and at least a portion of the reference surface, wherein the reference surface includes a texture thereon, and wherein the texture is configured for directing reflections from any outside surface, other than from the reference surface, away from the field of view of the first temperature sensor.

13. The photo-thermal targeted treatment system of claim 12, wherein a first measurement taken by the first temperature sensor is compared to a second measurement taken by the second temperature sensor for use in calibrating the first temperature measurement with respect to the second temperature measurement.

14. The photo-thermal targeted treatment system of claim 13, wherein the first and second measurements are taken in situ during the treatment protocol.

15. The photo-thermal targeted treatment system of claim 14, wherein the first and second measurements are used by the controller to modify the treatment protocol in progress.

16. The photo-thermal targeted treatment system of claim 15, wherein the first and second measurements are used by the controller to modify an initialization timing of the treatment protocol in accordance therewith.

17. The photo-thermal targeted treatment system of claim 15, wherein the first and second measurements are used by the controller to terminate the treatment protocol in accordance therewith.

18. The photo-thermal targeted treatment system of claim 12, wherein the texture is configured for directing radiation, other than from the reference surface, away from the field of view of the first temperature sensor.

19. The photo-thermal targeted treatment system of claim 18, wherein the texture includes a sawtooth pattern.

20. The photo-thermal targeted treatment system of claim 12, wherein the temperature measurement system is integrated into the photo-thermal treatment unit.

21. The photo-thermal targeted treatment system of claim 12, wherein a time response of the measured surface temperature is used to estimate the underlying dermis temperature, thereby providing a more accurate estimate of temperature of the sebaceous gland targeted by the photo-thermal targeted treatment system than would be possible without the temperature measurement system.

* * * * *